(12) United States Patent
Sutter et al.

(10) Patent No.: US 9,138,285 B2
(45) Date of Patent: Sep. 22, 2015

(54) COAGULATION FORCEPS WITH A TUBULAR SHAFT

(71) Applicant: Sutter Medizintechnik GmbH, Freiburg (DE)

(72) Inventors: Bert Sutter, Freiburg (DE); Thomas Dunz, Denzlingen (DE)

(73) Assignee: Sutter Medizintechnik GmbH, Freiburg (DE)

( * ) Notice: Subject to any disclaimer, the term of this patent is extended or adjusted under 35 U.S.C. 154(b) by 89 days.

(21) Appl. No.: 13/921,293

(22) Filed: Jun. 19, 2013

(65) Prior Publication Data

US 2013/0338668 A1  Dec. 19, 2013

(30) Foreign Application Priority Data

Jun. 19, 2012  (DE) .......................... 10 2012 012 167

(51) Int. Cl.
| | |
|---|---|
| A61B 18/14 | (2006.01) |
| A61B 18/12 | (2006.01) |
| A61B 18/18 | (2006.01) |
| A61M 1/00 | (2006.01) |
| A61B 18/00 | (2006.01) |

(52) U.S. Cl.
CPC ......... *A61B 18/1447* (2013.01); *A61B 18/1206* (2013.01); *A61B 18/1445* (2013.01); *A61B 18/18* (2013.01); *A61M 1/008* (2013.01); *A61B 2018/00589* (2013.01); *A61B 2218/007* (2013.01)

(58) Field of Classification Search
CPC .......................... A61B 18/1442; A61B 18/1445
USPC ................................. 606/49, 51, 52
See application file for complete search history.

(56) References Cited

U.S. PATENT DOCUMENTS

| | | | | |
|---|---|---|---|---|
| 3,807,406 | A * | 4/1974 | Rafferty et al. | 606/174 |
| 4,005,714 | A * | 2/1977 | Hiltebrandt | 606/51 |
| 4,985,030 | A * | 1/1991 | Melzer et al. | 606/51 |
| 5,891,142 | A * | 4/1999 | Eggers et al. | 606/51 |
| 6,059,783 | A * | 5/2000 | Kirwan, Jr. | 606/51 |
| 6,110,171 | A * | 8/2000 | Rydell | 606/51 |
| 6,293,946 | B1 * | 9/2001 | Thorne | 606/48 |
| 8,361,070 | B2 * | 1/2013 | Hanlon et al. | 606/51 |
| 2005/0187547 | A1 * | 8/2005 | Sugi | 606/48 |
| 2005/0222602 | A1 * | 10/2005 | Sutter et al. | 606/192 |
| 2006/0074416 | A1 * | 4/2006 | Hushka | 606/51 |

(Continued)

FOREIGN PATENT DOCUMENTS

DE   102006012558   9/2006

*Primary Examiner* — Joseph Stoklosa
*Assistant Examiner* — Jocelyn D Ram
(74) *Attorney, Agent, or Firm* — Volpe and Koenig, P.C.

(57) ABSTRACT

A coagulation forceps with a tubular shaft and with two forceps limbs and, which can both be movable or of which one is fixed, are uncovered on the gripping surfaces that face one another and serve for gripping tissue to be treated. At the distal ends, they have end surfaces, which contact a common plane, and are insulated on their outer sides that face away from one another, and provision is made for current connections for connection to a radiofrequency generator or to a current source for bipolar coagulation. Here, not only the gripping surfaces, but also the distal end surfaces of the forceps limbs and are uncovered and these uncovered end surfaces can be connected to uncovered outer surfaces of the forceps limbs and continuing said end surfaces such that tissue contacted by the two end surfaces and/or the outer surfaces can also be coagulated in a bipolar manner.

10 Claims, 7 Drawing Sheets

(56) References Cited

U.S. PATENT DOCUMENTS

| | | |
|---|---|---|
| 2006/0217708 A1* | 9/2006 | Sutter et al. .................... 606/51 |
| 2009/0138013 A1* | 5/2009 | Thorne et al. ................... 606/48 |
| 2010/0087814 A1* | 4/2010 | Desinger et al. ................ 606/45 |
| 2014/0276804 A1* | 9/2014 | Batchelor ....................... 606/45 |

* cited by examiner

COAGULATION FORCEPS WITH A TUBULAR SHAFT

INCORPORATION BY REFERENCE

The following documents are incorporated herein by reference as if fully set forth: German Patent Application No. 102012012167.9, filed Jun. 19, 2012.

BACKGROUND

The invention relates to a coagulation forceps with a tubular shaft and with two forceps limbs, which are uncovered on the gripping surfaces that face one another and serve for gripping tissue to be treated, have end surfaces, contacting a common plane, at their distal ends and are insulated on their outer sides that face away from one another, wherein provision is made for current connections for connection to a radiofrequency generator or to a current source for bipolar coagulation.

Such a coagulation forceps is known from DE 10 2006 012 558 A1. In the case of operations in which vessels have to be coagulated, for example in paranasal sinuses or optionally on spinal columns, a problem of such previously known coagulation forceps is that it is often not possible to grip a vessel to be coagulated with both gripping surfaces and coagulate it because e.g. surrounding bony tissue prevents the two gripping surfaces, i.e. the jaw of the instrument formed thereby, from being pushed sufficiently far over such a vessel. In such cases, coagulation of such a vessel or else of the surrounding tissue may be inadequate or it may be necessary to resort to monopolar coagulation with the problems associated therewith.

SUMMARY

There therefore is the object of developing a coagulation forceps of the type defined at the outset, by which it is also possible to coagulate tissue or blood vessels which cannot be gripped, or can only be gripped inadequately, by the two gripping surfaces or forceps limbs in a bipolar manner.

In order to achieve this apparently contradictory object, the coagulation forceps defined at the outset is characterized in that the two distal end surfaces of the forceps limbs are uncovered. As a result, the user is able, in the case of opened or at least slightly opened forceps limbs, to contact a tissue region or a blood vessel with the two end surfaces of these forceps limbs, without gripping them with the gripping surfaces, but nevertheless being able to coagulate them thereby.

Here, an preferred embodiment of the invention can provide for the uncovered end surfaces of the forceps limbs respectively to be connected to uncovered outer surfaces of these forceps limbs continuing said end surfaces or to be continued in said outer surfaces, which uncovered end surfaces extend onto the outer sides of the forceps limbs up to the insulation of the outer sides, which is recessed in relation to the end surfaces, provided there.

As a result, it becomes possible for the forceps limbs also to be pressed into slightly yielding tissue and for the desired, spatially restricted coagulation to be carried out, without, in the process, further regions being heated inadvertently and without it being necessary for tissue or vessels to be contacted by the gripping surfaces. The insulation on the outer side prevents too large tissue regions from being acted upon in the process.

It is preferred in this case if the uncovered outer surfaces on the outer sides of the forceps limbs are shorter than the uncovered gripping surfaces of the inner sides of the forceps limbs. Although these dimensions can also be approximately the same size, the shorter uncovered outer sides make coagulation by contacting tissue with these outer sides more effective. By way of example, the dimension of the uncovered outer surface in the direction of extent of the coagulation forceps and the forceps limbs can be a fifth, a quarter, a third, half, two-thirds, three-quarters, four-fifths or an intermediate value of the dimensions of the gripping surface.

For the best possible coagulation when contacting tissue or blood vessels with the uncovered end surfaces and, optionally, the uncovered outer surfaces continuing the latter, it is expedient if the uncovered end surfaces are flush with respect to one another when the forceps limbs are close to one another or if the uncovered end surface of the one forceps limb is protruding in relation to the uncovered end surface of the other forceps limb. If the two end surfaces lie flush with one another, they are both approximately level at the distal end of the coagulation forceps such that the user can also rotate the instrument as desired but is nevertheless able to coagulate successfully by contact. By contrast, if one of the forceps limbs and the end surface thereof projects beyond the other one, this creates an "overbite" which is particularly advantageous if the distal regions of the coagulation forceps are angled because it is then possible to treat a tissue structure, which has a termination surface extending perpendicular to the extent of the instrument and is contacted by the lower end surface and can then nevertheless be contacted by the angled instrument with the second end surface. Thus, this arrangement renders it possible wholly or partly to avoid a significant pivoting of the instrument, as would be necessary in the case of flush end surfaces.

A particularly expedient embodiment of the invention can provide for one of the forceps limbs to be fixed and the other forceps limb to be movable or pivotable relative thereto and for the fixed forceps limb preferably to have a suction channel on the outer side thereof that face away from the gripping surface, with the opening of said suction channel being recessed in relation to the uncovered end surface of this forceps limb. Coagulation forceps with only one movable forceps limb are easy to handle. Moreover, they render it particularly simple to provide a suction channel on the outer side of, in particular, the fixed forceps limb, as known from DE 10 2006 012 558 A1. In order, nevertheless, also to be able to employ the advantages of the coagulation option with the end surfaces and the outer sides of the forceps limbs continuing the former, the opening of the suction channel is, in this case, recessed so far in relation to the uncovered end surface, wherein the interspace between the opening of the suction channel and the end surface of this forceps limb can be uncovered and also be employed for coagulation.

The opening of the suction channel can be recessed in relation to the uncovered end surface on the outer surface of the fixed forceps limb by at least approximately half of the diameter or cross-sectional dimension of the suction channel or by the whole diameter or the whole cross-sectional dimension or by twice the diameter or twice the dimension of the cross section of the suction channel or an intermediate value thereof and the uncovered outer surface of this fixed forceps limb can be arranged adjacent to the opening of the suction channel in the distal direction. Here, the whole interspace between the opening of the suction channel and the end surface can be uncovered, but provision can also be made for another insulated region between the uncovered outer side of this fixed forceps limb and the opening of the suction channel if the uncovered outer side should be shorter than this distance.

The outer side of the forceps limb with the recessed opening of the suction channel can be designed as support surface for supporting the distal region of the coagulation forceps on tissue or on a bony structure. The coagulation forceps can be employed correspondingly safely because a support on the support surface contributes to being able to employ the instrument more precisely and without inadvertent movements.

The outer side that faces away from the gripping surface of at least one of the forceps limbs can, proceeding from the uncovered end surface, rise obliquely toward the proximal end and/or be arched in a convex manner and the uncovered end surface can be continued extending over this rising and/or arched region. This renders it easier to press the coagulation forceps and, in the process, the end sides of the forceps limbs somewhat into yielding tissue when the forceps limbs are opened in order to be able to carry out coagulation.

Here, it is also expedient for the geometry of the outer sides or the outer surfaces of the forceps limbs if, in the case of an arrangement with a fixed and a movable forceps limb, at least the movable forceps limb has the rise which proceeds from the end surface or the uncovered arch which proceeds from the uncovered end surface or continues the end surface or if both forceps limbs—whether both are movable or one of them cannot move—respectively have obliquely rising and/or arched continuations of their end surfaces toward sides that face away in relation to one another. Hence the advantages of such rising or arched uncovered surfaces can also be employed in a coagulation forceps in which one of the forceps limbs, preferably a forceps limb having a suction channel, is fixed.

An expedient design, in particular of the outer sides of the forceps limbs as well, emerges if the arch on the outer side of the forceps limb or limbs includes the whole uncovered outer surface or extends over the whole uncovered outer surface and, from a greatest distance from the associated gripping surface, falls back to a smaller distance toward the proximal end. Thus, in the region of the greatest distance between the outer surface and the gripping surface, the forceps limb has the greatest thickness in its uncovered regions, which thickness then decreases again toward the proximal end. Hence, particularly in yielding tissue, such an arch enables somewhat deeper pressing into such tissue by spreading open the forceps limbs and thereby achieves a coagulation of this tissue region.

The arch of the outer side near the end surface of at least one forceps limb can merge into the insulated region in its region that is decreasing from the greatest thickness of the forceps limb and be continued as far as a point of smallest thickness of the forceps limb and, from there, it can optionally be designed as increasing again. This results in a substantially restricted arched surface which, after pressing the coagulation forceps into tissue or after insertion into a tissue opening by spreading the forceps limbs, can easily be pressed into such tissue such that the desired coagulation can occur over the partly displaced tissue between the forceps limbs. Here, the two arches of the two forceps limbs are expediently mirror-symmetrical in relation to a plane between the two forceps limbs when the forceps limbs are close to one another or else closed such that the user practically always has corresponding conditions at the end surfaces and the continuations thereof when the coagulation forceps are rotated and said user can rotate the instrument as desired, depending on the formation of the operation field, but can nevertheless have the same coagulation conditions.

The forceps limbs can be angled upward in relation to the tubular shaft in the direction of the side that faces away from the handles and, in particular, the upper one of these two angled forceps limbs can protrude beyond the lower, more particularly fixed, forceps limb in the distal direction. Particularly in the case of such angled forceps limbs, the user is only able to contact a tissue surface extending at approximately right angles to the tubular shaft with both end sides of the forceps limbs if he pivots the instrument slightly upward. Such a necessity for pivoting can be avoided by the aforementioned measure, in which the upper one of the two oblique forceps limbs protrudes slightly further than the lower forceps limb.

A coagulation forceps, by which it is also possible to coagulate tissue or tissue regions which cannot be gripped, or cannot be gripped well, by the gripping surfaces of the forceps limbs and be clamped between the latter emerges, in particular, when combining individual or several of the above-described features and measures such that the coagulation forceps according to the invention can also be employed if blood vessels or tissue cannot or should not be gripped but a local bipolar coagulation should nevertheless be carried out. However, at the same time, the option of clamping blood vessels or tissues with the gripping surfaces and coagulating the former is maintained.

BRIEF DESCRIPTION OF THE DRAWINGS

In the following text, exemplary embodiments of the invention are described in more detail on the basis of the drawing. In a partly schematic representation.

DETAILED DESCRIPTION OF THE PREFERRED EMBODIMENTS

In the following description of several exemplary embodiments, parts corresponding in terms of their function are provided with corresponding reference signs, even in the case of a modified design.

A coagulation forceps, denoted by 1 in its entirety, has a tubular shaft 2 and two forceps limbs 3 and 4, which are uncovered on the gripping surfaces 5 that face one another and serve for gripping tissue to be treated (cf. FIG. 6) in order thereby to coagulate gripped tissue or a blood vessel in a bipolar manner.

At their distal ends, the forceps limbs 3 and 4 respectively have an end surface 6 that contacts a common plane and are provided with insulation 7, which is indicated by shading in the drawings, on the outer sides thereof that face away from one another, i.e. in the regions that face away from the gripping surfaces 5.

Here, it is possible to identify current connections 9 in the region of actuation handles 8, for the connection to a radiofrequency generator or a current source such that a bipolar coagulation can be carried out using the coagulation forceps 1.

Figures 5, 6:
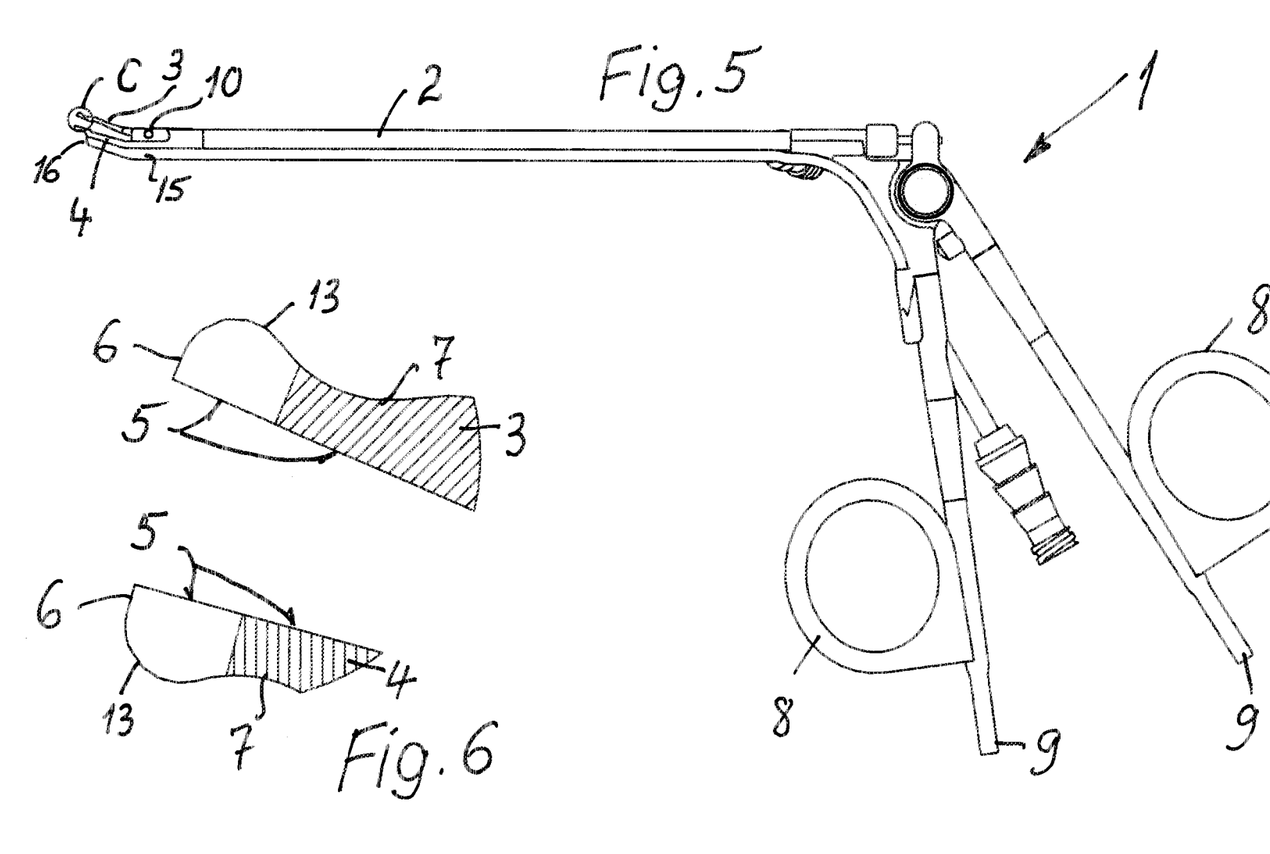
FIG. 5 shows an illustration corresponding to FIG. 3, wherein the forceps limbs are moved apart from one another by virtue of the only movable forceps limb being pivoted relative to the fixed forceps limb such that the gripping surfaces are distanced from one another, wherein a suction channel is arranged on the lower side of the fixed forceps limb.
FIG. 6 shows the detail of the distal end of the moved-apart forceps limbs, marked by the circle C in FIG. 5.

Provision is made in all exemplary embodiments for one of the forceps limbs, namely the forceps limb 4, to be fixed and for the other forceps limb 3 to be movable relative to this fixed forceps limb 4, for the purposes of which it is mounted on a pivot bearing 10, as known from DE 10 2006 012 558 A1. According to this, with the aid of the finger or actuation handles 8, relative pivoting of one of these actuation handles 8 relative to the other one can bring about the pivoting of the forceps limb 3 away from the forceps limb 4, as illustrated in FIGS. 5 and 6, where this pivoting has taken place.

However, it is also feasible that both forceps limbs 3 and 4 can be pivoted away from one another.

It is possible to identify, particularly in the magnified illustrations of FIGS. 2, 4, 6 and 8, that the distal end surfaces 6 of the forceps limbs 3 and 4 are uncovered in all exemplary embodiments.

Figure 9:
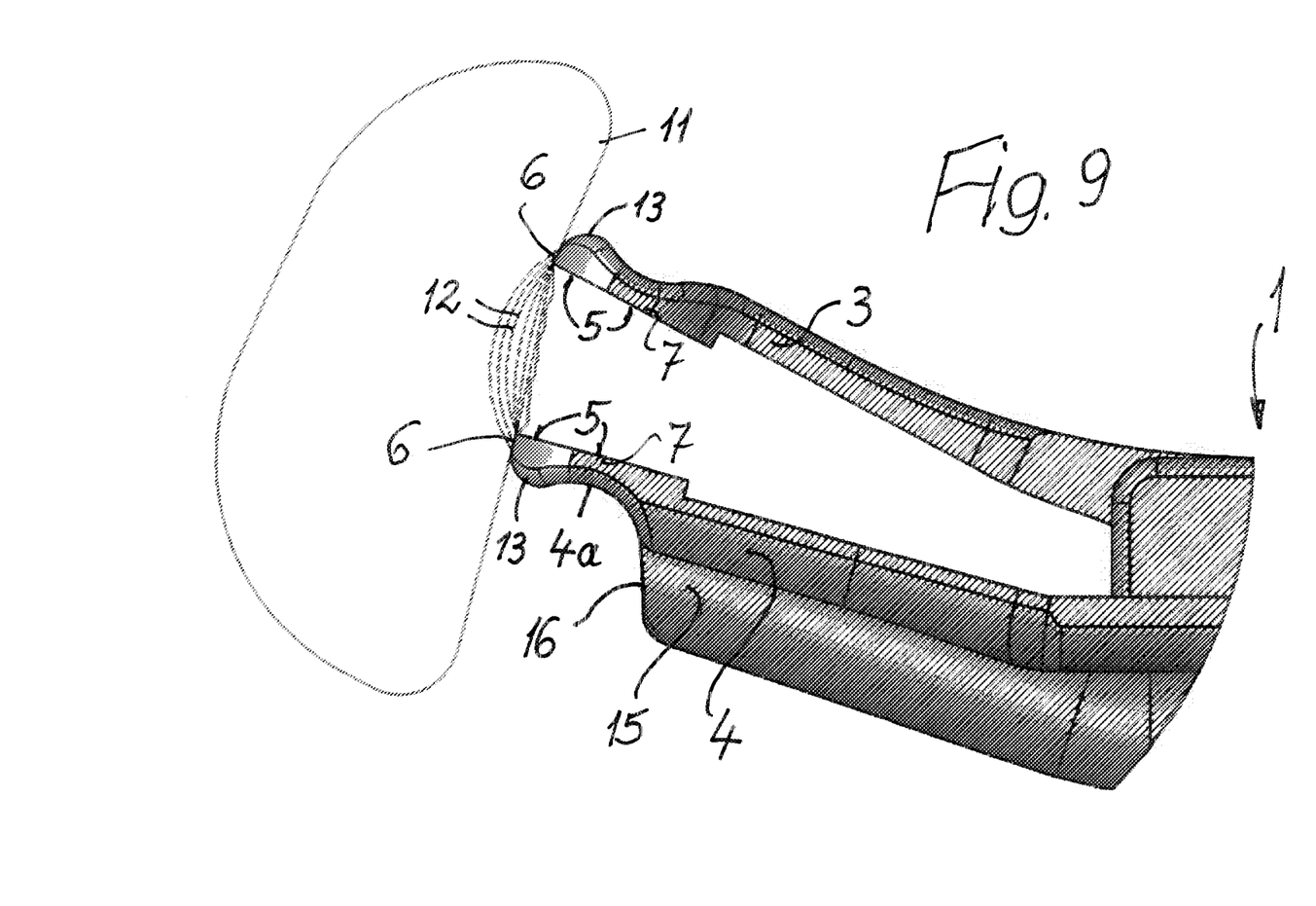
FIG. 9 shows, with a magnified scale, the forceps limbs of the coagulation forceps according to the invention in an open position when contacting tissue with the uncovered end surfaces, as a result of which the tissue is coagulated in bipolar fashion in its surface region between the two forceps limbs.

Hence, in accordance with FIG. 9, it is possible to coagulate tissue 11 on the surface by virtue of these uncovered end surfaces 6 contacting the tissue 11, without tissue needing to be gripped by the gripping surfaces 5. Thus, coagulation is also possible if the tissue 11 or blood vessels in difficult operation fields cannot be acted upon by the gripping surfaces 5, i.e. cannot be clamped between the latter. Nevertheless, an operator is able to coagulate a corresponding region by contacting it with the uncovered end surfaces 6. In FIG. 9, the current flow between the two end surfaces 6 is indicated schematically by dashed lines 12.

Provision is made in all exemplary embodiments for the uncovered end surfaces 6 respectively to be connected to uncovered outer surfaces 13 of the forceps limbs 3 and 4 continuing the former, which outer surfaces extend on the outer sides of the forceps limbs 3 and 4 as far as the insulations 7, which are recessed in relation to the end surfaces 6, provided there.

In accordance with all exemplary embodiments, the uncovered outer surfaces 13 on the outer side of the forceps limbs 3 and 4 are shorter than the uncovered gripping surfaces 5 on the inner sides of the forceps limbs, with this meaning the length in the direction of extent of the forceps limbs 3 and 4 and not the length of the surface or outer line. Here, it is furthermore possible to identify that the gripping surfaces 5 extend over a longer length range of the forceps limbs 3 and 4 than the outer surfaces 13, wherein the insulation 7 ends obliquely in accordance with FIG. 2 and ends in a plane extending at right angles to the gripping surfaces 5 in the other exemplary embodiments.

Figures 1, 2:
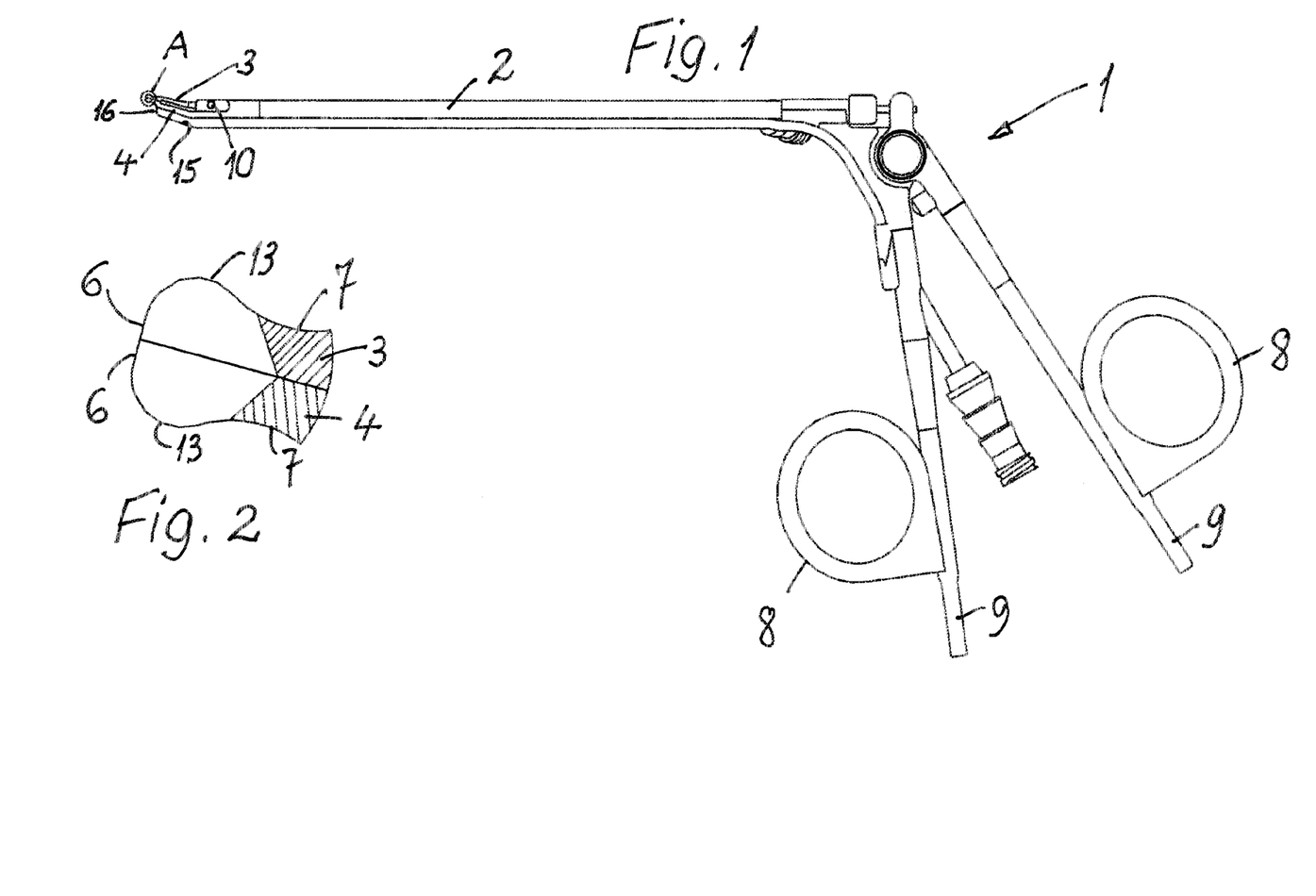
FIG. 1 shows a side view of a coagulation forceps according to the invention, with a tubular shaft and two forceps limbs in a closed position.
FIG. 2 shows, with a magnified scale, the detail denoted by the circle A in FIG. 1, namely the distal end regions of the forceps limbs, which are uncovered on their gripping surfaces, the end surfaces and some of the outer surfaces, wherein the insulation of the forceps limbs on the outer side is represented by shading and the length of the gripping surfaces is greater than the length of the uncovered region on the outer side.
Figures 3, 4:
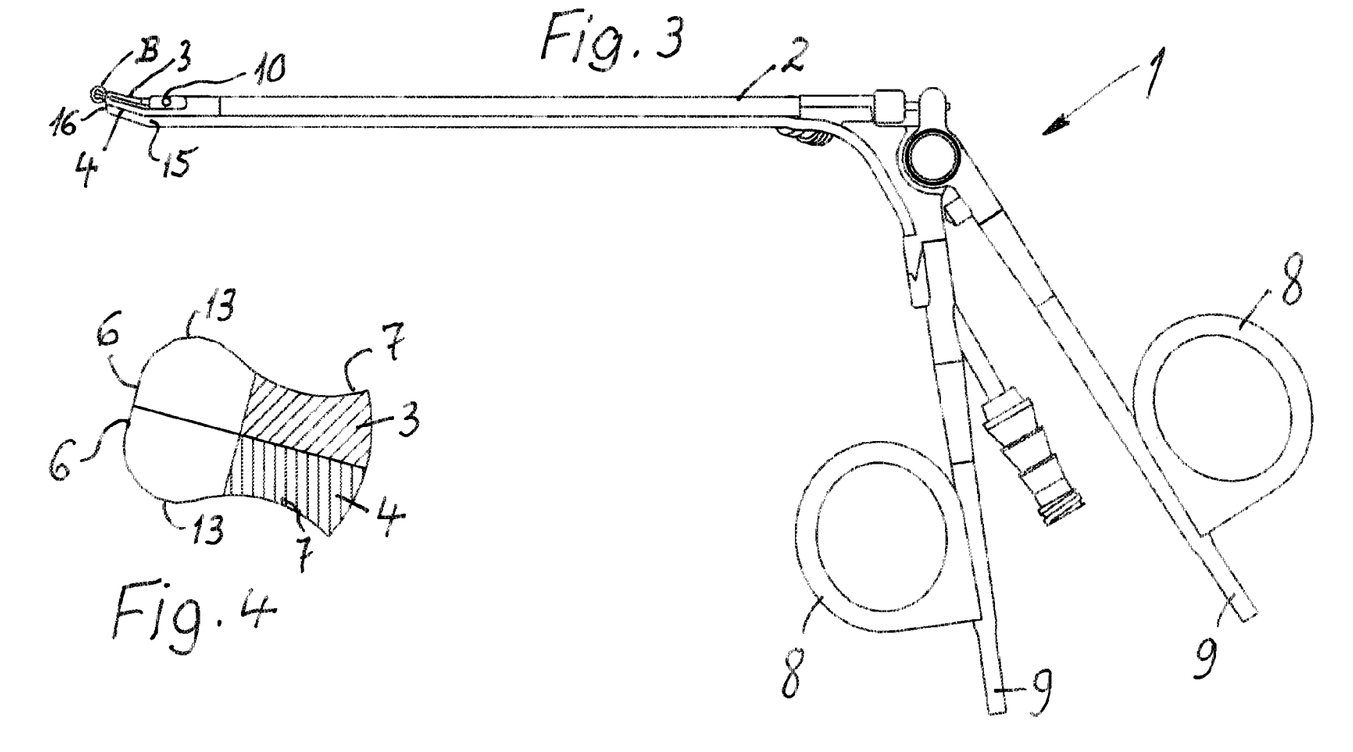
FIG. 3 shows an illustration corresponding to FIG. 1 of a modified exemplary embodiment.
FIG. 4 shows the detail marked by the circle B in FIG. 3, wherein the uncovered outer surfaces have a smaller extent than in the exemplary embodiment in accordance with FIG. 2.
Figures 7, 8:
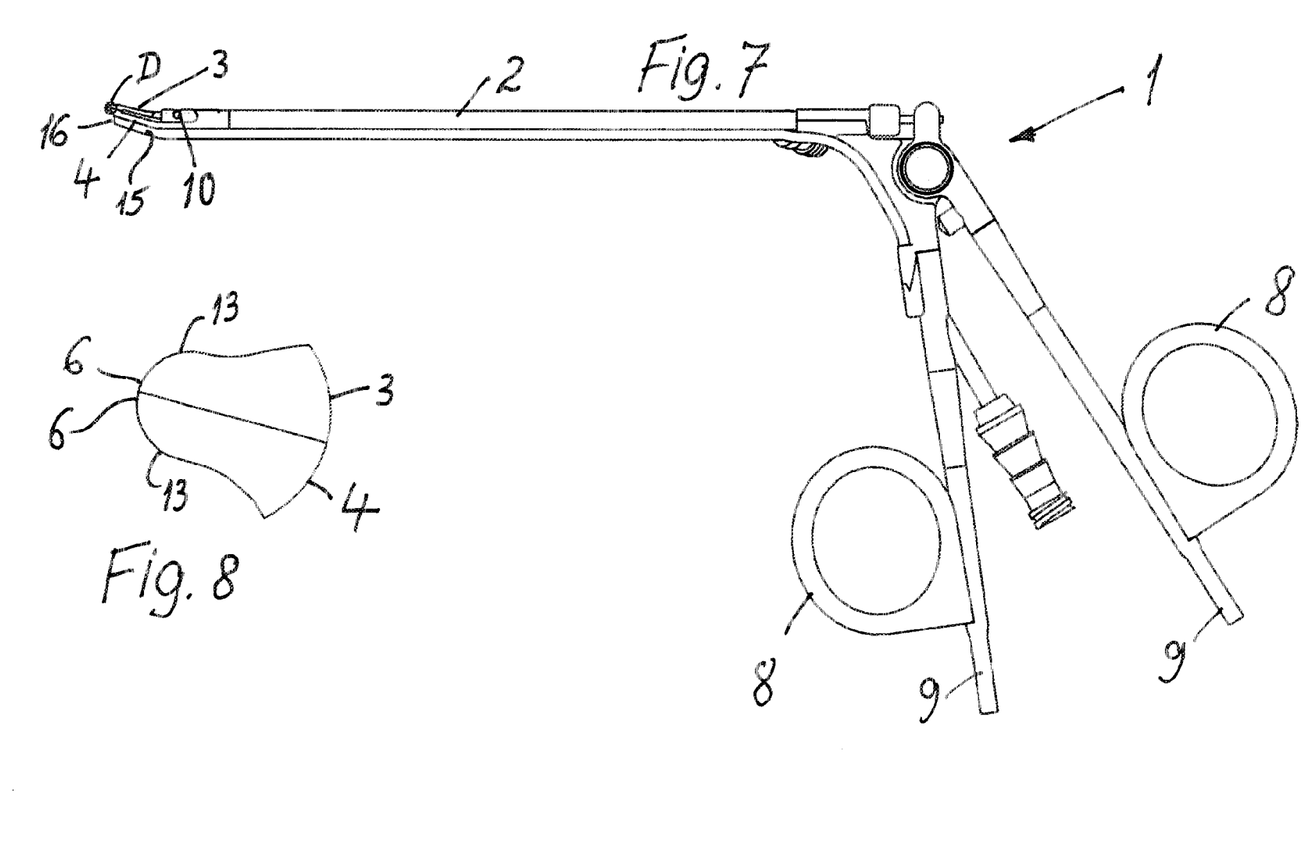
FIG. 7 shows an illustration corresponding to FIGS. 1, 3 and 5 of a modified embodiment of the coagulation forceps according to the invention, with closed forceps limbs.
FIG. 8 shows, with a magnified scale, the detail denoted in FIG. 7 by the circle D, wherein the outer sides of the forceps limbs have a less thick arch compared to the exemplary embodiments in accordance with FIGS. 1 to 6.

It becomes clear, in particular on the basis of FIGS. 2 and 4, that the uncovered end surfaces 6 lie flush with one another when forceps limbs 3 and 4 are close to one another or closed and that said end surfaces continue with a straight-lined region opposite one another; this also applying to the end surfaces 6 of FIG. 8 with a curved longitudinal section, but in this case the regions are curved. As a result, the use in accordance with FIG. 9 is particularly simple and can be independent of the rotation direction of the coagulation forceps 1, that is to say the user can coagulate such tissue 11 over an area by contacting it with the end surfaces 6, independently of how he selects the position of the coagulation forceps 1 in the rotation direction.

Figure 10:
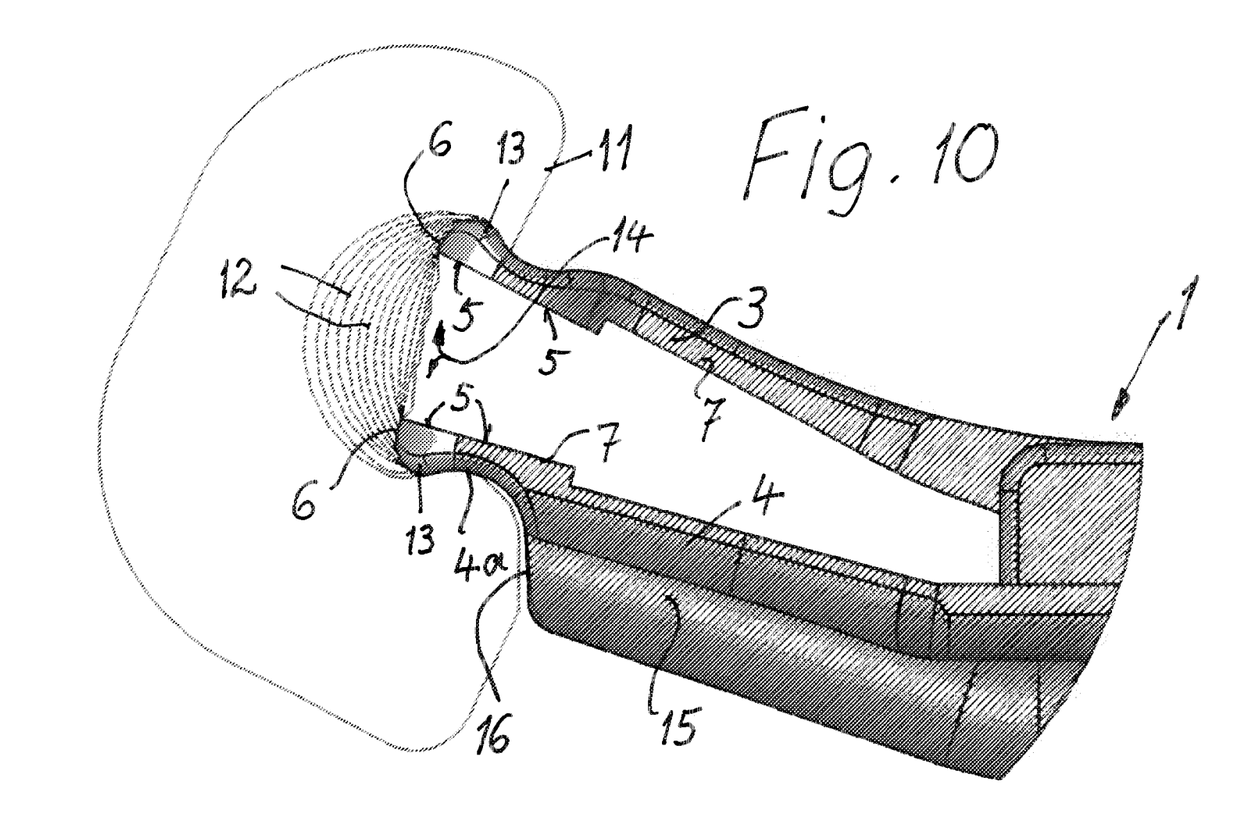
FIG. 10 shows an illustration corresponding to FIG. 9, in which the two spaced apart or opened forceps limbs, with the uncovered end surfaces and uncovered outer surfaces thereof, engage into a tissue recess, without gripping tissue or vessels, as a result of which the tissue recess is coagulated as indicated.

FIG. 10 illustrates that the uncovered outer surfaces 13 further extend the options for using the coagulation forceps 1. According to FIG. 10, these uncovered outer surfaces 13 can also be pressed into the tissue 11 such that the latter receives a recess due to its yielding, or tissue 11 could already have a recess 14, such that the edges thereof can, as illustrated in FIG. 10, be acted upon by the outer surfaces 13 in order to bring about bipolar coagulation in accordance with the dashed lines 12. Thus, in this case it is also possible to carry out coagulation with the coagulation forceps 1, without the gripping surfaces 5 having to take up tissue or blood vessels between them and contact the latter, which of course still is possible with this coagulation forceps 1 in accordance with the various exemplary embodiments. FIGS. 9 and 10 only show the additional options that emerge from the uncovered end surfaces 6 and the uncovered outer surfaces 13.

As already known from DE 10 2006 012 558 A1, provision is also made in all exemplary embodiments for the fixed forceps limb 4 to have a suction channel 15 on its outer side that faces away from the gripping surface 5, the opening 16 of which suction channel is recessed in relation to the uncovered end surface 6 of this fixed forceps limb 4 such that the outer surface 13 of the fixed forceps limb 4 is also available for coagulation in accordance with FIGS. 9 and 10.

The opening 16 of the suction channel 15 which has an approximately tubular design is recessed on the outer side of the fixed forceps limb 4 in relation to the uncovered end surface 6 thereof by more than the cross-sectional dimension of this suction channel 15 or of the tube forming the latter and the uncovered outer surface 13 is arranged adjacent to this opening 16 in the distal direction. Hence this distance between the opening 16 of the suction channel 15 and the end surface 6 is available for coagulation in accordance with FIG. 10.

Here, it can moreover be clearly identified in FIG. 10 that the outer side of the forceps limb 4 having the recessed opening 16 of the suction channel 15 simultaneously has or forms a support surface 4a for supporting the distal region of the coagulation forceps 1 on tissue or on a bony structure. As a result of the recessed opening 16 of the suction channel 15, a sufficiently large region and spacing remain to the end surface 6, which region and spacing can be used as such a support surface 4a, as illustrated in FIG. 10. The instrument 1 or the coagulation forceps 1 can be held and employed in a corresponding still manner during a treatment in accordance with FIG. 10.

Provision is made in all exemplary embodiments for the outer side that faces away from the gripping surface 5, and hence for the outer surface 13, proceeding from the uncovered end surface 6, to rise obliquely toward the proximal end and/or to be arched in a convex manner, wherein the uncovered end surface 6 is continued extending over this rising and arched region. This therefore results in a continuous uncovered region from the end surfaces 6, via the outer surfaces 13, up to the insulation 7. The coagulation in accordance with FIG. 10 can be carried out correspondingly well. Here, the arches of the outer surfaces 13 can form a type of undercut in a tissue recess 14 if the tissue 11 yields accordingly.

In the exemplary embodiments in accordance with FIGS. 1 to 6, the arch on the outer side of the forceps limb or limbs 3 and 4 includes the whole uncovered outer surface 13 and extends over this uncovered outer surface 13, as a result of which a greatest distance to the gripping surface 5 is formed, i.e. where provision is made for a greater thickness in the region of the gripping surfaces 5 than adjacent thereto. From this greatest distance to the gripping surface 5, the uncovered outer surface 13 then falls back again toward the proximal end of the instrument to a smaller distance. Precisely this protruding arch of the outer surfaces 13 adjacent to the end surfaces 6 renders it possible for these outer surfaces 6 to be slightly pressed into the tissue 11 in order to enable the undercut of the recess 14, indicated in FIG. 10, with a correspondingly effective bipolar coagulation.

By contrast, in the exemplary embodiment in accordance with FIGS. 7 and 8, provision is made for a further rise toward the distal end after the end surface 6 and the continuing arch of the outer surface 13, which may be advantageous for some cases with e.g. slightly conical recesses 14.

In the exemplary embodiments in accordance with FIGS. 1 to 6, the arch of the outer side near the end surface 6 of the forceps limbs 3 and 4 merges into the insulated region in its region which is decreasing from the greatest thickness of the forceps limb 3 and 4 and can continue as far as a point of a smallest thickness of the forceps limbs 3 and 4 and can, in accordance with FIGS. 2, 4 and 6, thereafter also increase again, but wherein the insulation 7 already begins in the region of the decreasing thickness.

In a manner not illustrated in any more detail, the gripping surfaces 5 can serve for gripping around a tissue region or for gripping blood vessels in order to coagulate these in a bipolar manner. However, additionally, it is also possible to contact tissue 11 on the surface and coagulate it in a bipolar manner or else press into the tissue and engage into a recess 14 or even increase or even create said recess by corresponding pressure, in order to be able to coagulate a larger region in a bipolar manner, without vessels or tissue needing to be between the gripping surfaces 5.

Figure 11:
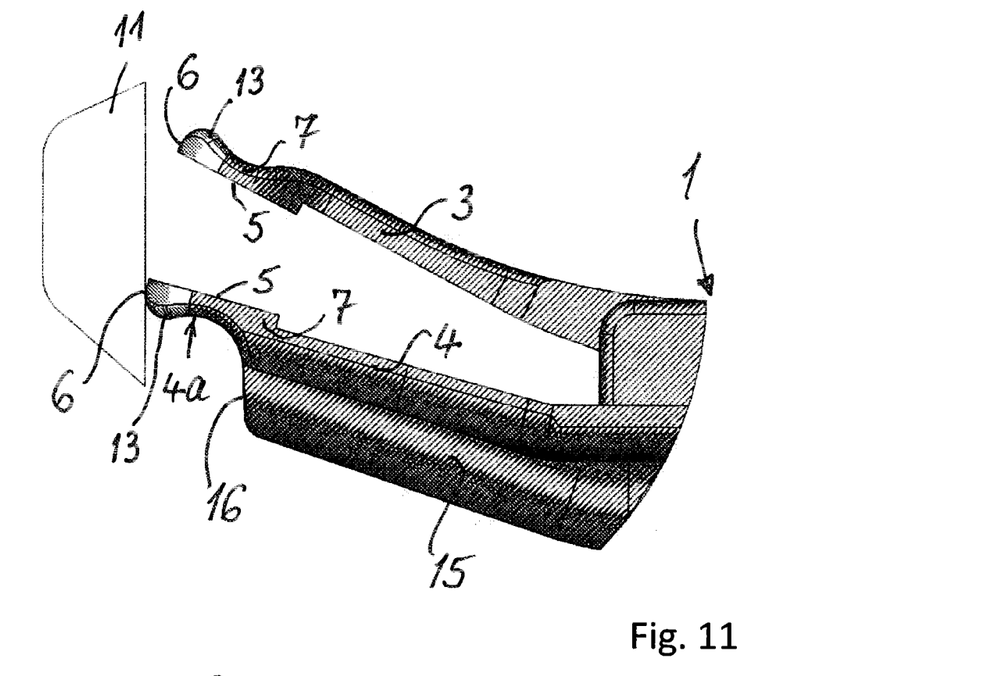
FIG. 11 shows an illustration, approximately corresponding to FIGS. 9 and 10, of two spaced apart and opened forceps limbs, which extend obliquely in relation to the tubular shaft and have a corresponding length with approximately flush end surfaces, in relation to a tissue region extending at approximately right angles to the tubular shaft, in which, when this tissue region is contacted by the lower forceps limb, the upper forceps limb does not reach the tissue.

While, in FIG. 9, the surface of the tissue 11 is arranged approximately at right angles to the profile of the forceps limbs 3 and 4 and these therefore bring about simultaneous contact with the tissue 11 and hence coagulation, the same end of the instrument with the forceps limbs 3 and 4 is illustrated in FIG. 11, wherein, however, the surface of the tissue 11 is arranged at approximately right angles to the profile of the tubular shaft 2. For coagulation in accordance with FIG. 9, the tubular shaft must therefore, in this situation, be pivoted slightly upward in the region of the handles 8 so that the upper forceps limb 3 also reaches the tissue 11.

Figure 12:
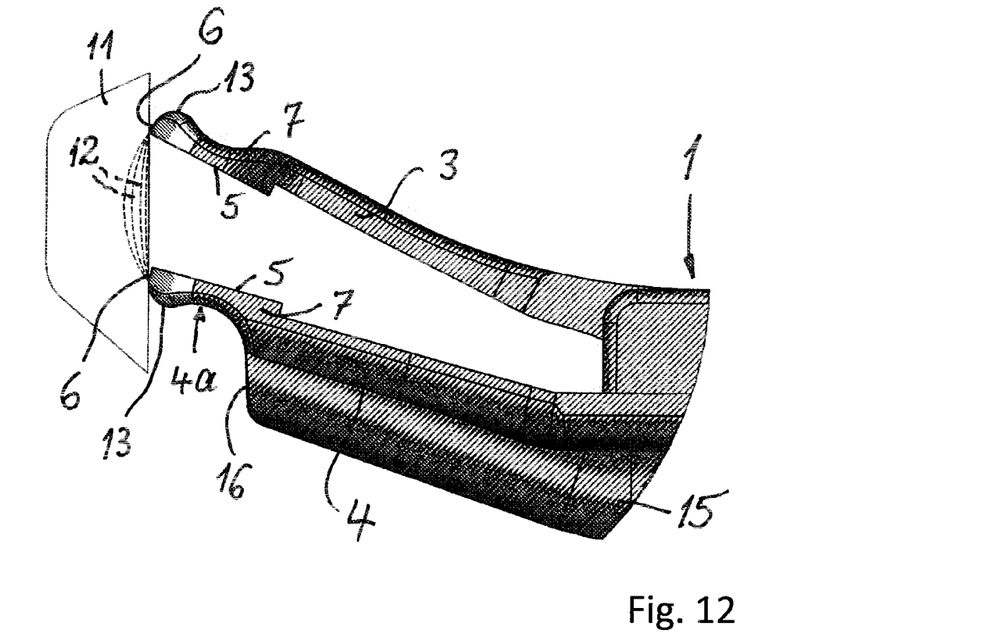
FIG. 12 shows an illustration corresponding to FIG. 11, in which the upper forceps limb has a greater length than the lower forceps limb, i.e. the end surfaces of the two forceps limbs do not lie flush in relation to one another, such that the upper forceps limb, simultaneously with the lower forceps limb, contacts and coagulates the tissue region.

So that such pivoting of the instrument and the coagulation forceps 1 can be avoided but tissue 11 in the position in accordance with FIGS. 11 and 12 can nevertheless be coagulated by both uncovered end sides or end surfaces 6 of the forceps limbs 3 and 4, even though the forceps limbs 3 and 4 project obliquely upward relative to the extent of the tubular shaft 2, the upper forceps limb 3 is slightly longer than the lower forceps limb 4 in the exemplary embodiment according to FIG. 12. When comparing FIGS. 11 and 12, it is clearly possible to identify that this nevertheless still renders it possible to coagulate tissue 11 in the position in accordance with FIGS. 11 and 12 in the case of a tubular shaft 2 extending at approximately right angles to this tissue 11 due to the overbite of the upper forceps limb 3 in relation to the lower forceps limb 4.

The coagulation forceps 1 with a tubular shaft 2 and with two forceps limbs 3 and 4, which can both be movable or of which one is fixed, are uncovered on the gripping surfaces 5 that face one another and serve for gripping tissue to be treated. In particular, at their distal ends, they have end surfaces 6, which contact a common plane, and are insulated on their outer sides that face away from one another, wherein provision is made for current connections 9 for connection to a radiofrequency generator or to a current source for a bipolar coagulation. Here, not only the gripping surfaces 5, but also the distal end surfaces 6 of the forceps limbs 3 and 4 are uncovered and these uncovered end surfaces 6 can be connected to uncovered outer surfaces 13 of the forceps limbs 3 and 4 continuing said end surfaces such that tissue 11 contacted by the two end surfaces 6 and/or the outer surfaces 13 can also be coagulated in a bipolar manner.

The invention claimed is:

1. A coagulation forceps comprising a tubular shaft with two forceps limbs, each having an inner facing surface, outer sides, and a distal end surface, wherein the inner facing surfaces are uncovered, an insulation is located on the outer sides, current connections are provided on the two forceps limbs for connection to a radiofrequency generator for bipolar coagulation, and at least the distal end surfaces of the forceps limbs are uncovered, wherein each of the two forceps limbs has an uncovered arched continuation of the distal end surface thereof that extends on the outer sides towards a proximal end thereof, wherein an arch of each of said forceps limbs defines a maximum distance between the outer side and the inner facing surface of the forceps limb, said maximum distance being located nearer to the distal end than to the proximal end of the forceps limb, and wherein the distance between the outer side and the inner facing surface of the forceps limb decreases from a location of the maximum distance towards the proximal end of the forceps limb, wherein the uncovered distal end surfaces extend to the outer sides of the forceps limbs up to the insulation, the insulation is recessed in relation to the distal end surface, and wherein along a longitudinal extension of the forceps limbs, the uncovered surfaces on the outer sides of the forceps limbs are shorter than the uncovered surfaces on the inner facing surfaces which form gripping surfaces of the forceps limbs.

2. The coagulation forceps as claimed in claim 1, wherein the uncovered distal end surfaces (6) are flush with respect to one another when the forceps limbs approach one another.

3. The coagulation forceps as claimed in claim 1, wherein the uncovered distal end surface (6) of the one forceps limb (3) projects over the distal end surface (6) of the other forceps limb (4).

4. The coagulation forceps as claimed in claim 1, wherein the arch of the outer side of the gripping region of at least one forceps limb merges into an insulated region in a downwardly directed region and as far as a point of a smallest thickness of the limb and increases again from there.

5. The coagulation forceps as claimed in claim 1, wherein the forceps limbs (3, 4) are angled upward in relation to the tubular shaft (2) in a direction of the side that faces away from a plurality of handles connected to the forceps limbs (8).

6. The coagulation forceps as claimed in claim 5, wherein an upper one of the two angled forceps limbs protrudes beyond a lower, fixed one of the forceps limbs (4) in the distal direction.

7. A coagulation forceps comprising a tubular shaft with two forceps limbs, each having an inner facing surface, outer sides, and a distal end surface, wherein the inner facing surfaces are uncovered, an insulation is located on the outer sides, current connections are provided on the two forceps limbs for connection to a radiofrequency generator for bipolar coagulation, and at least the distal end surfaces of the forceps limbs are uncovered, wherein each of the two forceps limbs has an uncovered arched continuation of the distal end surface thereof that extends on the outer sides towards a proximal end thereof, wherein an arch of each of said forceps limbs defines a maximum distance between the outer side and the inner facing surface of the forceps limb, said maximum distance being located nearer to the distal end than to the proximal end of the forceps limb, and wherein the distance between the outer side and the inner facing surface of the forceps limb decreases from a location of the maximum distance towards the proximal end of the forceps limb, wherein one of the forceps limbs is fixed and provided with a suction channel opening on the outer side thereof, wherein the suction channel opening is recessed in relation to the uncovered distal end surface.

8. The coagulation forceps as claimed in claim 7, wherein the suction channel opening is recessed in relation to the uncovered end surface by approximately half of a diameter of the suction channel or by a diameter or a cross-sectional dimension of the suction channel or an intermediate value, and the uncovered surface situated on the outer side on the fixed forceps limb is arranged adjacent to the suction channel opening.

9. The coagulation forceps as claimed in claim 8, wherein the outer side of the forceps limb (4) with the recessed opening (16) of the suction channel (15) forms a support surface (4a) for supporting a distal region of the coagulation forceps (1) on tissue or on a bony structure.

10. The coagulation forceps as claimed in claim 7, wherein a second of the two forceps limbs is a movable forceps limb.

\* \* \* \* \*